United States Patent [19]
Ying

[11] Patent Number: 5,356,625
[45] Date of Patent: Oct. 18, 1994

[54] MICROGRANULAR PREPARATION USEFUL IN THE DELIVERY OF BIOLOGICALLY ACTIVE MATERIALS TO THE INTESTINAL REGIONS OF ANIMALS

[75] Inventor: Thomas K. S. Ying, Rowville, Australia

[73] Assignee: Enzacor Properties Limited, St. Helier, Channel Islands

[21] Appl. No.: 316,354

[22] Filed: Feb. 27, 1989

[30] Foreign Application Priority Data

Aug. 28, 1986 [AU] Australia .............................. PH 7715
Aug. 17, 1987 [WO] PCT Int'l Appl. .................. PCT/AU87/00270

[51] Int. Cl.$^5$ ..................... A61K 37/54; A61K 37/48; A61K 9/50; A61K 33/00
[52] U.S. Cl. .................................. 424/94.1; 424/94.3; 424/94.61; 424/94.63; 424/94.65; 424/438; 424/458; 424/460; 424/490; 424/492; 424/646; 424/647; 424/648; 424/643; 424/722
[58] Field of Search .................. 424/438, 458–462, 424/490–498, 94.1, 94.65, 94.63, 94.61, 94.3, 646–648, 643, 722; 514/963–965, 52

[56] References Cited

U.S. PATENT DOCUMENTS

| | | | |
|---|---|---|---|
| 3,656,997 | 4/1972 | Cordes | 424/94.21 |
| 3,789,117 | 1/1974 | Tsujino | 424/94.21 |
| 3,803,304 | 4/1974 | Antonides | 424/94 |
| 4,230,687 | 10/1980 | Sair et al. | 514/725 |
| 4,332,790 | 6/1982 | Sozzi et al. | 424/38 |
| 4,447,412 | 5/1984 | Bilton | 424/16 |

FOREIGN PATENT DOCUMENTS

| | | |
|---|---|---|
| 268704 | 10/1963 | Australia . |
| 59876/69 | 2/1971 | Australia . |
| 10299/76 | of 1977 | Australia . |
| 504584 | 12/1977 | Australia . |
| 516072 | 4/1979 | Australia . |
| 0077956A1 | 1/1983 | European Pat. Off. . |
| 2419722 | 10/1979 | France . |

OTHER PUBLICATIONS

International search report for prior counterpart application No. PCT/AU87/00270.

Primary Examiner—Jacqueline Stone
Attorney, Agent, or Firm—Christensen, O'Connor, Johnson & Kindness

[57] ABSTRACT

A microgranular preparation having a core of biologically active material that is encapsulated by a water soluble film that is covered by an enteric coating of either an alkali soluble, acid insoluble polymer or a high molecular weight polymer whose structure is substituted with or contains windows of fatty acids or other material capable of being solubilized by intestinal juices. Useful for protecting pH sensitive and other biologically active materials from inactivation or contact with the stomach or rumen, and releasing the same in active form in the intestinal tract, particularly the duodenum.

29 Claims, 2 Drawing Sheets

MICROGRANULAR PREPARATION USEFUL IN THE DELIVERY OF BIOLOGICALLY ACTIVE MATERIALS TO THE INTESTINAL REGIONS OF ANIMALS

This is a continuation-in-part of international application No. PCT/AU87/00270, filed Aug. 28, 1986.

TECHNICAL FIELD

The present invention relates to preparations useful in the delivery of biologically active materials to the intestinal regions of animals, and particularly to a microgranular preparation in which the biologically active material is immobilized, preferably within a swellable gel matrix, in a core that is encapsulated within a water-soluble mechanical barrier that is surrounded by an enteric coating susceptible to digestion in the intestine but not the stomach or rumen. The invention further relates to a method of producing the microgranular preparation, and to methods of therapeutically administering the microgranular preparations to humans and other animals.

BACKGROUND OF THE INVENTION

The absorption of biologically active materials from the alimentary tract takes place mainly in the intestines.

Many biologically active materials are acid labile, and on exposure to acidic conditions are denatured, or chemically modified such that they lose activity. This presents a problem when the biologically active molecules are orally administered to animals, as for example are many pharmaceutical and veterinary compounds, which need to pass through the stomach.

The stomach region of animals is highly acidic, by virtue of hydrogen ions produced by the parietal cells of the stomach lining. The pH of this region maybe as low a 1 pH unit. Consequently many biological compounds are irreversibly denatured, modified and/or destroyed before they reach the intestinal regions where adsorption takes place.

A number of useful therapeutic compounds and essential minerals are stomach irritants. Particularly, aspirin, $Fe^{2+}$, $Fe^{3+}$, $Zn^{2+}$, $K^+$, cause stomach irritation when orally administered. This irritation can lead to ulceration of the stomach lining. This disadvantage offsets the therapeutic advantages of these compounds.

Lack or imbalance of digestive enzymes in animals, due to genetic disorders or pancreatic disease, may be treated by the oral administration of enzymes. However, many of these enzymes are acid labile and are irreversibly denatured in the acidic region of the stomach, before they reach the intestinal regions. Consequently, large doses of enzymes have to be given, making this treatment ineffective and expensive.

Biologically active materials are often denatured on passage though the rumen of ruminant animals, where alkaline pH conditions are encountered. This also may act as a barrier to the successful use of orally administered therapeutic agents.

It is an object of the present invention to provide a preparation, and method of delivering biologically active materials to the intestines of animals, the preparation eliminating or substantially reducing the loss of biological activity due to the acidic conditions of the stomach, or the alkaline conditions of the rumen.

SUMMARY OF THE INVENTION

The invention provides, in one aspect, a microgranular preparation having a core that contains one or more biologically active materials in an immobilized form, the core being encapsulated within a water soluble film that is covered by an enteric coating of either an alkali soluble, acid insoluble polymer or a high molecular weight polymer whose structure is substituted with or contains windows of fatty acids or other material capable of being solubilized by intestinal juices. The subject microgranular preparation protects pH sensitive and other biologically active materials from inactivation in or contact with the stomach or rumen, yet releases them for action in the intestinal tract, particularly the duodenum.

The biologically active material may be selected from among pharmaceutical and veterinary compounds, enzymes, vitamins, proteins, vaccines, and amino acids. Representative examples include iron, zinc, and potassium salts, vitamin $B_{12}$, riboflavin, methionine, $\beta$-galactosidase, and bromelin. Such biologically active materials are preferably immobilized in the core within a swellable gel matrix, e.g., formed from k-carrageenan, gelatin, alginate, cellulose or its derivatives, or gel forming synthetic polymers. A representative water soluble film for encapsulating such cores is gelatin. A representative alkali soluble, acid insoluble polymer for the outer, enteric coating is cellulose acetate phthalate. A representative high molecular weight polymer for the enteric coating is butyl methylacrylate substituted with $C_{12-24}$ fatty acids. The subject microgranules typically range in average size from about 25 to about 500 $\mu$m, and preferably from about 50 to about 350 $\mu$m.

In a second aspect, the invention provides a method for producing the subject microgranular preparation, by immobilizing one or more biologically active materials within a core, microgranulating the immobilized biologically active molecules, encapsulating the microgranules with a water-soluble mechanical barrier, and coating the encapsulated microgranules with either an alkaline-soluble acid-insoluble polymer, or a high molecular weight polymer whose structure is substituted with or contains windows of fatty acid or other material capable of being solubilized by intestinal juices.

In a third aspect, the invention provides a method of treating a condition or disease caused by, e.g., enzyme deficiency or pathogenic bacteria binding to intestinal receptors, in humans and other animals, by administering a therapeutically effective amount of the subject microgranular preparation wherein the core contains, e.g., $\beta$-galactosidase or a protease. Representative embodiments include methods for increasing animal growth in preweaned animals, particularly pigs, by administering an effective amount of the subject microgranular preparation wherein the core contains immobilized $\beta$-galactosidase. As another example, scour in piglets is treated by administering the subject microgranular preparation in which the core contains immobilized $\beta$-galactosidase or a protease such as bromelin.

DETAILED DESCRIPTION OF THE PREFERRED EMBODIMENT

Figure 1:
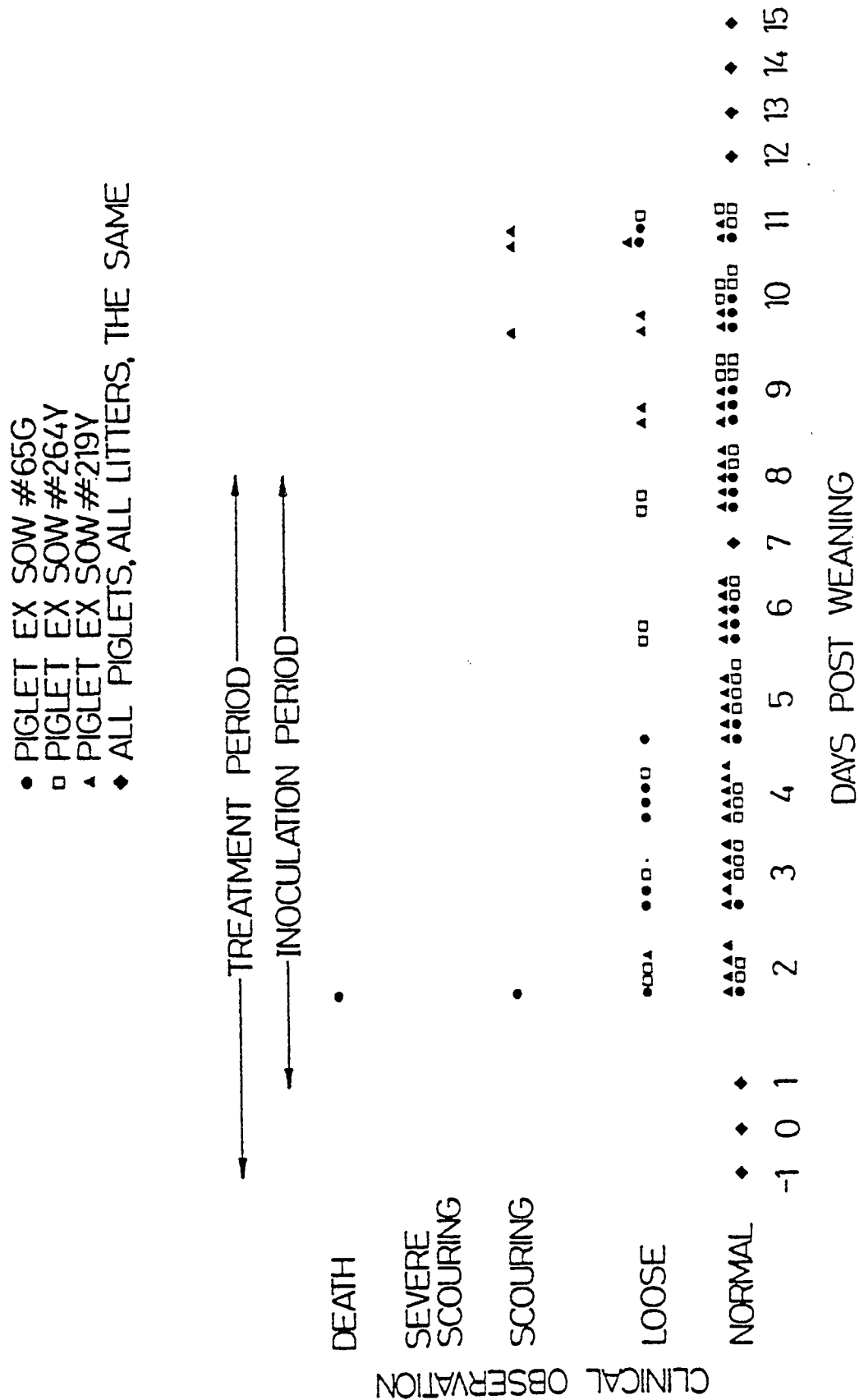
FIGS. 1 and 2 are scatter diagrams of scouring severity in bromelin-treated and untreated piglets, respectively, showing the incidence and severity of scouring is reduced when piglets are treated with the subject microgranular preparation.

According to one aspect of the present invention there is provided a microgranular preparation having a core comprising one or more biologically active materials in an immobilized form, the core being encapsulated within a water soluble film and coated with an enteric coating comprising an alkali soluble, acid insoluble polymer, or a high molecular weight polymer, whose structure is substituted with or contains windows of fatty acid or other material capable of being solubilized by intestinal juices.

Biologically active materials refers to pharmaceutical and veterinary compounds; enzymes such $\beta$-galactosidase and bromelin; vitamins such as vitamin B12; metal ions such as $Fe^{2+}$, $Fe^{3+}$, $Zn^{2+}$, $K^+$, antibiotics, antiseptics and pharmaceutically acceptable salts thereof; proteins, vaccines, amino acids and microorganisms.

The term "immobilized form" refers to the biologically active material being immobilized within a gel-like material, enclosed within a semi-permeable membrane, adsorbed onto adsorbing agents or bound to chelating agents.

Biologically active materials may be immobilized, for example, by any of the following methods:
(a) The entrapment method—The incorporation of biologically active materials into the core of gel-like materials or enclosure within a semi-permeable membrane;
(b) The cross-linking method—Intermolecular cross-linking of the biologically active materials utilizing cross-linking reagents; or
(c) The carrier binding method—The physical or chemical binding of the biologically active materials to a water insoluble substance by ionic and/or covalent bonds.

The immobilization is carried out such that the biologically active material retains activity either while immobilized or when released.

The entrapment of biologically active materials within a core may be carried out by admixture of the biologically active materials with agents capable of forming a gel under certain conditions, such that the biologically active materials are entrapped within the formed gel matrix. Examples of gel forming agents include k-carrageenan, alginic acid, gelatin, cellulose or its derivatives or various gel-forming synthetic polymers such as polyamides or Chitosan.

If an adsorbing agent is used it is preferably microfined activated charcoal.

Chelating agents if used may include EDTA, its salts or derivatives, or high molecular weight hydrophilic polymers such as polyacrylamides or high molecular weight salts capable of dissociating their ionic bond in aqueous solution or aqueous/hydrophilic solvent.

Encapsulation involves the deposition of a thin film or chemical barrier over the core enabling physical separation of the core of each microgranule and its environment. This film or barrier is water soluble. An example of a compound forming a suitable barrier is gelatin.

The enteric coating is preferably cellulose acetate phthalate. However, any other acid resistant, alkali soluble polymer may be utilized.

Butyl methacrylate or other high molecular weight polymers may be substituted with or contain windows of stearic acid or any other fatty acid derivative, or other material, capable of being solubilized by bile juice. Preferably the fatty acids are $C_{12-24}$.

The immobilization of biologically active materials within a gel is a most advantageous feature. Particularly, the gel matrix restricts the accessibility of denaturing agents, such as organic solvents used in the application of an enteric coating (an acid insoluble, alkali soluble coating such as cellulose acetate phthalate). A significant proportion of the biologically active material immobilized within the gel matrix is thus ultimately available for catalytic or other activity.

The gel matrix in which the biologically active materials may be immobilized is porous and permeable. Accordingly, when the gel is exposed to aqueous conditions, such as the environment of the duodenum, the gel swells due to the entry of intestinal juice into the gel matrix, and the biologically active materials may be released and pass out of the gel for catalytic or other activity.

Microgranules of a very small particle size, in the order of 50 $\mu$m to 500 $\mu$m, may be produced according to the practice of the present invention. Particularly, biologically active material immobilized within a gel, or in a solution capable of forming a gel, are easy to handle and process, and may be subject to gentle procedures to produce microgranules of the desired small particle size. For example, a gel containing biologically active material may be extruded through a sieve of very small pore size, or may be freeze dried to give particles of the desired size. Alternatively, biologically active material in a solution capable of forming a gel, may be sprayed through a suitable nozzle to form fine droplets which pass into a solution which causes the droplets to gel, thereby immobilizing the biologically active material within the formed gel matrix. The size of the granules formed in this manner is determined by the pore size in the nozzle and the pressure at which the solution is atomized. In contrast, such results cannot be obtained by prior art approaches. In the prior art, biologically active materials such as enzymes are merely mixed with conventional binding agents which are not susceptible to the above treatments to produce microgranules of the desired particle size.

Microgranules of a small particle size are most desirable, as they may be evenly distributed through feed, and allow rapid release of biologically active material when they reach the intestine, due to the increased surface area of the microgranules.

The provision of a water soluble barrier about the core, provides protection against denaturation caused by organic solvents used during application of enteric coatings. Because of the protective nature of the gel matrix mentioned earlier, significant maintenance of biological activity of the biologically active material is achieved.

The microgranular preparation of the present invention enables pH sensitive biologically active material to be protected from inactivation in the stomach or the rumen, yet be available for action in the intestinal tract, particularly the duodenum. When the microgranular preparation reaches the alkaline regions of the intestine of monogastric animals, the outer coating is dissolved, or the fatty acid windows are digested. Intestinal juice is then able to pass to the water soluble coating causing it to be degraded. This exposes the core, causing it to swell and release the biologically active material.

In ruminant animals, a high molecular weight polymer, such as butylmethacrylate with fatty acid windows is appropriate as an over coating and allows the passage of the microgranular preparation through the rumen and the stomach. In the intestinal regions, particularly the duodenum, the fatty acid windows are digested by lipases, thus allowing the water soluble coating to be degraded and the core exposed, causing it to swell and release the biologically active material.

As the skilled person will readily appreciate, the thickness of the coatings of the water soluble film and the alkali soluble polymer or high molecular weight polymer interrupted by a fatty acid or similar emulsifiable substance, and the core size, governs the rate at which the biologically active materials are available, and additionally the locality within the intestine where the biologically active materials are available.

According to another aspect of the invention there is provided a microgranular preparation as defined previously wherein the core contains β-galactosidase. Such a preparation is useful as a growth promotant for pre-weaned animals, particularly preweaned piglets. Additionally the preparation is useful for treating scour in piglets.

The carbohydrate present in sow milk is largely lactose. Lactose requires digestion to simple sugars, namely glucose and galactose, to allow absorbtion from the lower part of the intestinal tract. By supplementing extra β-galactosidase at the beginning of the intestinal tract, utilizing the above mentioned microgranular preparation, sow milk may be digested more completely causing a weight gain in piglets.

β-galactosidase deficiency in piglets, humans (manifested as lactose intolerance) or other animals may be treated by the administration of the aforementioned microgranular preparation containing β-galactosidase. β-galactosidase is thereby liberated in the intestines, this facilitating lactose digestion.

Undigested lactose in the lower part of the intestinal tract forms an ideal culture for colonic bacteria to multiply and ferment, forming gas and lactic acid. This results in watery acidic diarrhoea. This condition is known as scour. Severe scour may lead to loss of body fluid and electrolyte imbalance causing dehydration and death.

A further approach to treating scour, within the scope of the present invention, utilizes the microgranular preparation of the present invention containing a protease, such as bromelin. Bromelin, on release in the small intestine, detaches pathogenic microorganisms from intestinal receptors, thereby alleviating scour.

According to another aspect of the invention there is provided a method for increasing animal growth in preweaned animals, particularly pigs, which involves the administration of an effective amount of a microgranular preparation as defined previously wherein the core contains β-galactosidase in an immobilized form.

According to a further aspect of the invention there is provided a method for the treatment of scour in piglets which comprises the administration of a therapeutically effective amount of the microgranular preparation herein before described wherein the core contains β-galactosidase or a protease such as bromelin.

The present invention is particularly useful for the administration of acid labile materials such as vitamin B12 and riboflavine to animals including humans.

Additionally, materials which cause stomach irritation such as aspirin or iron, may be safely delivered to animals, including humans, using the microgranular preparation of the present invention. These materials are consequently not exposed to the digestive tract until they reach the alkaline regions of the intestines.

According to a still further aspect of the present invention there is provided a method for protecting acid sensitive biologically active materials from destruction and/or inactivation in the stomach or rumen, comprising the administration of a microgranular preparation having a core comprising one or more biologically active materials in an immobilized form, the core being encapsulated within a water soluble film and coated with either an alkaline soluble acid insoluble polymer, or a high molecular weight polymer whose structure is substituted with or contains windows of fatty acid or other materials capable of being solubilized in intestinal juices.

The microgranular preparation of the present invention may be orally administered to humans or animals in association with a pharmaceutically acceptable or veterinarily acceptable carrier or excipient. For example, the microgranular preparation may be administered with water, kaolin, talc, calcium carbonate, lactose, sodium chloride, copper sulphate, zinc sulphate, ferrosulphate, magnesium sulphate, potassium iodide, sulphur, potassium chloride, selenium and/or vitamins such as biotin, choline chloride, nicotinamide, folic acid or vitamins A, D3, E, K, B1, B2, B6 and B12.

The microgranular preparations may be administered as an aqueous acidic solution, a suspension, in a tablet or capsule form, as a paste, or in association with food or feed stocks.

Examples of appropriate animal feed stocks include one or more of the following: maize, wheat middling, soya bean meal, fish meal, grass meal, skim milk, tricalcium phosphate, malt, corn, rice, milo, whey, or alpha-meal.

According to a still further aspect of the present invention there is provided a process for the production of a microgranular preparation as hereinbefore described comprising the steps of:

(a) immobilizing one or more biologically active materials within a core, (b) microgranulating the immobilized biologically active material, (c) encapsulating the microgranules with a water soluble mechanical barrier, and (d) coating the microgranules of step (c) with either an alkaline soluble acid insoluble polymer, or a high molecular weight polymer whose structure is substituted with or contains windows of fatty acids or other materials cable of being solubilized by intestinal juices.

Preferably the microgranules are spray coated with the water soluble mechanical barrier of step (c) and the coating of step (d).

Figure 2:
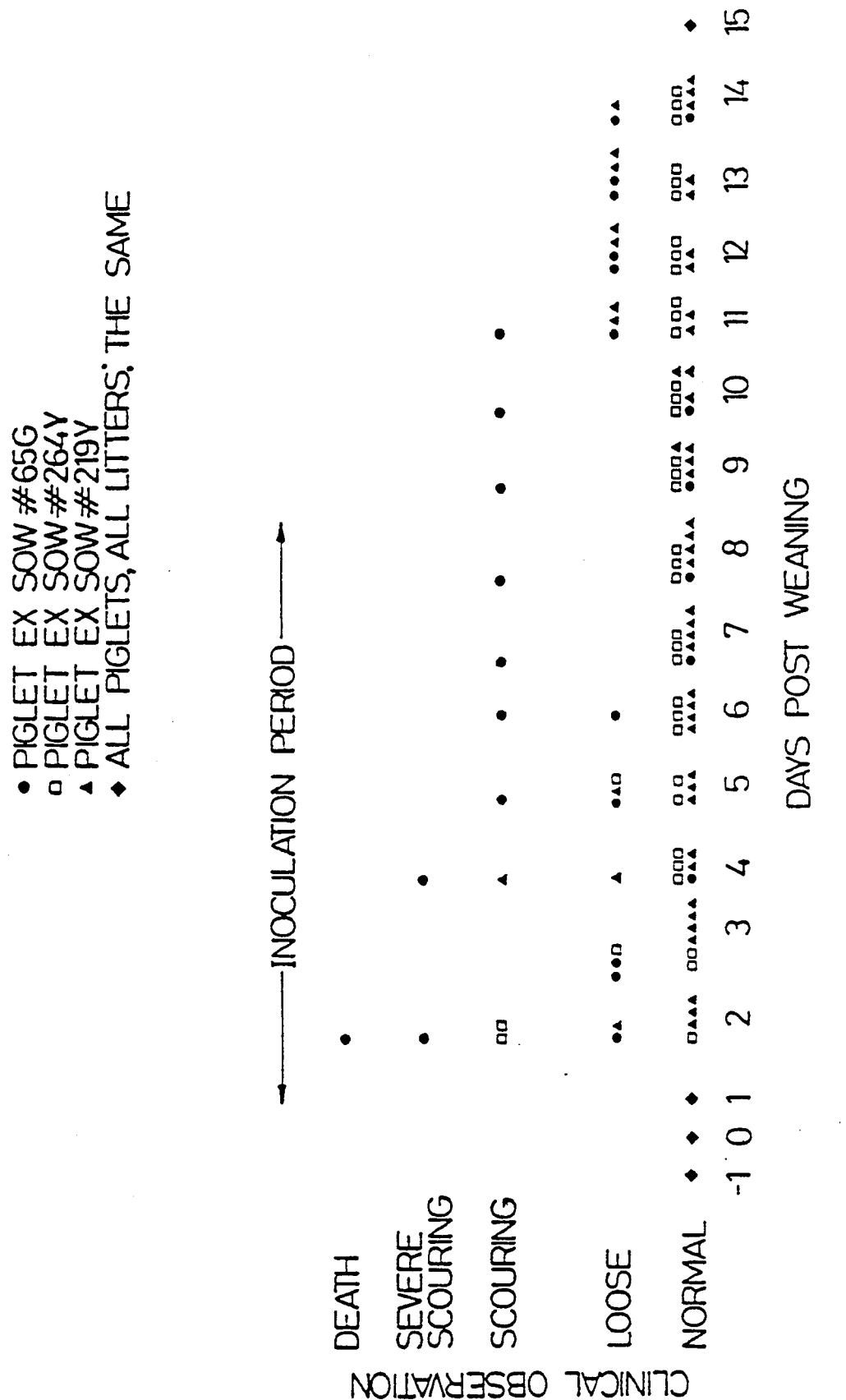

The present invention will now be described by way of example only, with reference to the following Examples and figures in which:

FIG. 1 shows a scatter diagram of scouring severity in bromelin treated piglets; and FIG. 2 shows a scatter diagram of scouring severity in untreated piglets.

EXAMPLE 1

Method of preparation of the microgranular preparation of the present invention (a) 2%–5% w/v of k-carrageenan is mixed with purified water at a temperature of 65° C. until dissolution of the k-carrageenan is achieved. This solution is cooled to 50° C.

(b) 1% w/v of a biologically active material is dissolved in isotonic phosphate buffer solution (40% 0.067M Na $H_2PO_4$ + 60% 0.067M $Na_2HPO_4$) at pH 6 at 50° C. This solution is added to solution (a) and homogenized at 500 $H_2$ for 15 minutes. 2–5% w/v of ionized calcium in water is then added to the solution and the resulting solution is homogenized for a further hour at 50 $H_2$ and then cooled to 20° C. giving a gel, liquid cell beads and an aqueous phase.

(c) The resulting gel, liquid cell beads and aqueous phase are cooled to 5° C., decanted, filtered and freeze dried. The freeze dried material is milled to give a granule size of 25–100 microns, and then washed with a hardening agent such as 2.5% w/w glutaraldehyde or formalin.

Alternatively, the gel-phase of step (b) is extruded and sprayed through 50 μm size pores at 3 kP/cm² and dropped 1–5 meters into a hardening agent such as 2.5% w/w gluteraldehyde or formalin thus causing granule formation.

(d) The granules are then filtered and washed with a softening agent such as glycerol. Any film softener may be used.

(e) The resulting granules are filtered, fluidised and heat dried at 40° C.

(f) The granules of the preceding step are sprayed coated with 1–2% w/v of gelatin in water solution, at 40° C.

(g) An acid resistant alkali soluble coating is then spray coated on the granules. The coating comprises:
6% w/w cellulose acetate phthalate
30% w/w isopropanol
0.5% w/w caster oil
and acetone to 100% w/w.

(h) As an alternative to step (g) a high molecular weight polymer whose structure in interrupted by a film of fatty acid or similar emulsifiable substances is spray coated onto the granules until the final weight is 105% w/w. The coating comprises:
3% w/w butyl methylacrylate
0.5% w/w dibutyl phthalate
0.05% w/w stearic acid
and ethylacetate to 100% w/w.

In step (a) k-carrageenan can be substituted with any gel forming agent such as alginic acid, gelatin, cellulose or its derivatives.

In step (b), calcium can be substituted with any other alkaline metal ions such as: K, $Rb^{2+}$, $Cs^+$, $Mg^{2+}$, $Sr^{2+}$, or bi- or tri- valent metal ions such as $Al^{3+}$, $Mn^{2+}$, $Ba^{2+}$, $Co^{2+}$, $Ni^{2+}$, $Zn^{2+}$, $Pb^{2+}$, etc. or $NH_4+$ ions or aliphatic amines or aromatic diamines such as triethylamines, methylenediamines, ethylamines, hexamethylenendiamines, etc.

EXAMPLE 2

The preparation of microgranules containing Vitamin $B_2$ (Riboflavine)

Method of preparation

1. Mix 7500 mg of British Pharmacopoea grade riboflavine with 5000 ml 0.3% glacial acetic acid solution. Heat in a water bath and shake until dissolved.

2. Mix 250 g of k-carrageenan with 5000 ml purified water at 65° C. until dissolution of carrageenan is achieved. This solution is cooled to 50° C. then mixed with the riboflavine solution.

3. The resulting gel/solution is then homogenised at 500 rpm for 15 minutes.

4. Add 5 l of 10% calcium chloride in distilled water to the gel/solution, which is then homogenized for 1 hour at 50 rpm. Cool to 5° C. and decant the gel phase.

5(a) 100 g of the decanted gel is freeze dried and granulated to give granules of approximately 100 μg.

5(b) The remainder of the gel phase if filtered and sprayed through 50 μm size pores at 3 /cm into 2.5% glutaraldehyde at a height of 3 meters.

6. Filter the granules of 5(b) and wash with 0.5% glycerol in water solution. The resulting granules are filtered, fluidized and heat dried at 40° C. Collect all granules.

7. The granules in the preceding step are spray coated with a 2% gelatin solution in water at 40° C. until the final weight is 104% w/w.

8. The granules are then spray coated with 3% butyl methacrylate, 0.15% dibutyl phthalate, 0.05% stearic acid in ethyl acetate solution until the final weight is 105% w/v.

9. Sieve the granules so that the average size of the granules is less than 500 microns.

TEST GRANULES

In vitro testing 1. 5 grams of "Test Granules" and 5 grams of "Control Granules" are placed in separate 6 cm × 6 cm nylon cloth bags.

2. The bags are sealed and submerged for 2 hours in a dilute Hydrochloric Acid solution—having a pH of 1, and stirred at 60 rpm.

3. The bags are then transferred from the acid solution, rinsed under running water for 30 minutes, and drip dried.

4. 200 ml of rumen fluid is collected through an opening in a fistula cow.

5. The two test bags are suspended in rumen fluid and incubated for 24 hours at 37° C.

6. Both bags are washed, then dried at 40° C.

7. The contents of each bag is weighed and assayed for riboflavine content.

Results

No Control Granules remain in the nylon cloth bag.

4.52 grams Test Granules were recovered from the nylon bags which contains the Test Granules. The loss of 0.48 g of Test Granules is probably due to breakdown of those microgranules which were not properly formed during the preparation method.

From assay result of 1 gram of rumen juice treated Test Granules, it was calculated that 4.52 grams of the Test Granules in the bag contain a total of 114 mg Riboflavine. 4.52 grams of untreated granules contain approximately 114 mg Riboflavine.

Two grams of the Test Granules were reintroduced into a nylon bag and suspended in 100 ml. of duodenum fluid collected from an abbatoir and incubated at 37° C. The granules disintergrated within two hours.

Assay method

1. The rumen juice treated Test Granules are discharged into 100 ml of ethyl acetate 50%/50% water solution and homogenised at 500 rpm for one hour.

2. The solvent phase is decanted and the aqueous phase retained.

3. The procedure is repeated three times.

4. 3 ml of glacial acetic acid is then added to the final aqueous phase. The mixture is heated in a water bath with frequent shaking until dissolved, filter through No. 1 Wattman filter paper and diluted to 1000 ml. 5 ml of 0.1M sodium acetate is added and the subsequent solution diluted to 50 ml with water. The absorbance of the resulting solution is measured with a maximum at about 444 nm. The content of riboflavine is calculated, taking 323 as the value of A (1% 1 cm) at the maximum of about 444 nm.

EXAMPLE 3

Microgranular preparation containing Methionine

Method of preparation

Microgranules containing methionine are prepared by the method of Example 2, with the exception that 30 grams of DL-Methionine, Food Grade, is used in Step 1. Granules containing methionine are hereinafter referred to as "Test Granules". "Control Granules" are formed according to the method of Example 2.

In Vitro Testing 1. 5 grams of "Test Granules"; and 5 grams of "Control Granules" are placed in separate 6 cm×6 cm nylon cloth bags.

2. The bags are sealed and submerged for 2 hours in dilute hydrochloric acid solution having a pH of 1, and stirred at 60 rpm.

3. The bags are transfer from the acid solution and rinsed under running water for 30 minutes, then dripped dry.

4. Collect 200 ml of rumen fluid are collected through an opening in a fistula cow.

5. The two test bags are suspended in the rumen fluid, and incubated for 24 hours at 37° C.

6. Both bags are washed and dried at 40° C.

7. The content of the bags are weighed and assayed methionine content.

Result

No Control Granules remain in the nylon cloth bag.

4.40 grams of Test Granules were recovered from the nylon bag which contained the Test Granules. The loss of 0.6 g of Test Granules is presumably due to the breakdown of defective microgranules.

From assay results of 1 gram of rumen juice treated Test Granules, it was calculated 4.40 gram of the Test Granules contains a total of 563 mg methionine, 4.4 g of untreated granules contain 536 mg methionine.

Two grams of the Test Granules were reintroduced into a nylon bag and suspended in 100 ml. of duodenum fluid collected from an abbatoir and incubated at 37° C. the granules were found to disintegrate within two hours.

Assay method

1. The rumen juice treated Test Granules are discharged into a 500 ml glass stopped flask. 200 ml of ethyl acetate 50%/50% water solution is added and homogenised at 500 rpm for one hour.

2. The solvent phase is decanted to retain the aqueous phase.

3. The procedure is repeated three times.

4. The final aqueous phase is made up to 20 ml with water. 10 gram dibasic potassium phosphate, 4 gram monobasic potassium phosphate and 4 gram potassium iodide were added and mixed well to dissolve.

5. Exactly 100 ml 0.1N iodine were added: the flask stoppered: mixed well: and allowed to stand for 30 minutes, then the excess iodine was titrate with 0.1N sodium thiosulphate. A blank determination and necessary corrections are made. Each ml of 0.1N iodine is equivalent to 7.461 mg of DL-Methionine.

EXAMPLE 4

Growth promotion in preweaned piglets

Piglets were given 2 ml of a paste containing the following:
   Vitamin $B_1$:5 mg
   Vitamin $B_2$:2 mg
   Vitamin $B_6$:8 mg
   Vitamin $B_3$:8 mg
   and the microgranular preparation of the present invention wherein the core contained $\beta$-galactosidase (300 F.C.C. LU).

The paste was administered on the day of birth and on the fifth day post partum.

Piglets given the above treatment showed an increased weight gain when compared with untreated piglets. Additionally, the incidence of scour was greatly reduced in piglets who received the microgranular preparation.

EXAMPLE 5

The prevention and treatment of scour in piglets

E. coli bacteria with K88 pili (K88+ E. coli) are responsible for a large proportion of neonatal and post-weaning scours in pigs. These bacteria must bind to intestinal receptors before they can cause disease.

In vitro experiments have indicated that the protease bromelin is extremely effective in degrading the K88 binding activity of the intestinal (glycoprotein) K88 receptor. This receptor is only expressed on the mucosal surface of the intestines of pigs of K88 susceptible phenotype.

The experiment shown hereunder illustrates the effectiveness of the microgranular preparation of the invention in the treatment of scours in piglets.

METHODS

Pigs

Three mated gilts were purchased from Werribee Animal Research Institute. The K88 phenotypes of the gilts were determined by capsule tests (Chandler, 1986). One pig (#65G) was found to be strong K88-adhesive (susceptible to infection), one weakly K88-adhesive (#264Y) and one K88-non-adhesive (#219Y). Litter sizes from these sows were 7, 7 and 9 piglets, respectively.

The gilts farrowed within 3 days of each other, and the piglets were weaned at about 3 weeks of age. Four piglets from each of the first two litters and 5 of the remaining litter were selected at random and treated daily with the microgranular preparations of the present invention containing bromelin (0.04% w/w). All other piglets remained untreated.

Treatment

Bromelin containing microgranules were orally administered (2 g/dose) in low pH carboxymethyl cellulose buffer, using a 10 ml syringe. Bromelin treatment was performed 1–2 h prior to feeding. The first dose of Bromelin was given on the day prior to weaning, and on eight successive days thereafter.

Inoculation

Massive inoculations (approx. $5 \times 10^9$ E. coli/day) of each of 5 strains of K88+ E. coli were administered daily. Four strains had been isolated from fatal cases of K88 colibacillosis. These strains were all serogroup 0149. They had been stored lyophilized since isolation, 1–5 years previously. The remaining K88+ E. coli was recently isolated from a non fatal case of scouring on a local piggery (serogroup 0 untypable). The bacteria were suspended from sheep blood agar (5% v/v) into phosphate buffered saline (PBS, pH 7.2). The piglets were, orally inoculated with the bacteria just prior to feeding.

Assessment of scouring

The health or degree of infection of the piglets was assessed by
(i) liveweight; liveweights taken prior to feeding were assessed for each piglet 17 times in the three week period from weaning to slaughter.
(ii) scouring; a subjective assessment of the clinical condition of the animal was made as follows:
normal: no symptoms of diarrhoea or dehydration
loose: faeces obviously more liquid than normal. No evidence of dehydration.
scouring: faeces liquid and profuse scouring, with evidence of debilitation and dehydration.
(iii) bacterial infection; the proportion of haemolytic (hly+) bacterial colonies evident when faecal material was plated onto sheep blood agar was determined.

Assessment of K88 phenotype

Scrapings of the mid-intestine were collected at autopsy from the boars to which the gilts has been mated. Similarly, sows and piglets were assessed for phenotype by constructing an adhesion pattern of five equi-distant sites along the small intestines obtained at autopsy. Piglets were slaughtered four weeks after weaning. The K88 phenotype of intestine scrapings was assessed by enzyme immunoassay (KPEIA, Chandler et al., 1986).

RESULTS

Severe scouring (and deaths) following K88+ E. coli inoculation were only evident in the piglets born to the K88-adhesive phenotype sow (#65G). Piglets from this litter were similarly K88-adhesive, although they were probably heterozygotes (i.e. carrying only single dominant gene for K88 receptor expression). Piglets from the weakly adhesive sow (#264Y) were variable in receptor activity but were less active than those from sow #65G. Piglets from the K88-non adhesive sow (#219Y) were also K88-non adhesive.

A scatter diagram indicating the daily assessments of scouring and the litter from which the piglets originated are shown in FIGS. 1 (bromelin treated piglets) and 2 (untreated piglets). Both the incidence and severity of scouring appeared to be lower in the bromelin treated piglets, although one piglet from each group died within 24 hours of weaning. Both these piglets were born to sow #65G. Ten recordings of "scouring" or severe scouring were made in the treatment/inoculation period, nine of these were made in piglets not receiving bromelin. Scouring became more evident in the bromelin treated group only after the completion of the inoculation/treatment period.

Assessment of the extent of infection in piglets by estimating the proportion of Hly+ colonies in platings of rectal swabs was found to be of little use, probably because the massive daily inoculations led to high proportions of Hly+ colonies in apparently unaffected piglets. The organisms were probably colonizing the large bowel of these piglets; a site where they do little harm.

Similarly, daily gains in liveweight were of little use in assessing possible benefits attributable to bromelin. The transitory scours observed amongst the piglets of low genetic susceptibility (piglets of the litters from sows #264Y and #219Y), did little to affect liveweight gains.

Piglets of the susceptible sow (#65G), as expected, were more severely affected by the bacterial challenge. Death of one piglet in each treatment group left only two piglets in the untreated group. Weight gain of one of these piglets was severely affected by the challenge, the other was not. None of the three bromelin treated piglets remained severely affected by the bacterial challenge.

This experiment indicates that K88 receptor activity can be modified in vivo by oral inoculation of microgranules containing bromelin immediately before weaning, and in the subsequent week when infection is likely to occur. Such microgranular preparations appeared to reduce the clinical symptoms of the disease.

Further experiments carried out by us indicate that piglets treated with the microgranular preparation of the invention which contains bromelin, show a 28% decrease in the incidence of scour, compared to untreated piglets.

This approach to the prevention or treatment of colibacillosis may provide an alternative to the use of antibiotics in intensive piggeries. As approximately 10 million pigs die annually from colibacillosis (Walters and Sellwood, 1984), treatment with microgranules containing a protease may be most advantageous to the pig industry.

The above experiment uses the protease bromelin. Although our experiments have shown bromelin to be the most effective protease for degrading the K88 receptor, it is to be understood that other proteases. Combinations of protease or enzymes acting to destroy or alter glycoproteins may be used in this aspect of the present invention. Examples of other proteases which may be utilized are: trypsin, fungal protease p23, subtilisin, proteinase K, and other fungal and bacterial proteases.

A number of other pathogenic bacteria are known, or are believed to bind to intestinal receptors. Examples of such bacteria are Salmonella, Shigella and streptococcus. Proteases encapsulated within the microgranular preparation of the present invention may be used to treat infections with such bacteria in animals and man.

The subject microgranular preparations, when formulated as described above, will typically be packaged with printed instructions specifying their use for treating an actual or potential condition or disease, e.g., β-galactosidase deficiency, by orally administering the preparation to a human or other host.

The embodiments of the invention in which an exclusive property or privilege is claimed are defined as follows:

1. A microgranular preparation having a core comprising one or more biologically active materials, the core being concentrically encapsulated within a water-soluble, organic solvent-insoluble film consisting essentially of gelatin, and an enteric coating comprising a polymer which is insoluble in acid but soluble in alkali or intestinal juice.

2. A microgranular preparation as claimed in claim 1, wherein the core comprises one or more biologically active materials immobilized within a gel matrix.

3. A microgranular preparation as claimed in claim 2, wherein the gel matrix is formed from k-carrageenan, gelatin, alginate, cellulose or its derivatives, or synthetic polymers.

4. A microgranular preparation as claimed in claim 1, wherein the microgranules have a size between about 25 and about 500 μm.

5. A microgranular preparation as claimed in claim 4, wherein the microgranules have a size between about 50 and about 350 μm.

6. A microgranular preparation as claimed in claim 1, wherein the biologically active material is selected from the group consisting of pharmaceutical and veterinary compounds.

7. A microgranular preparation as claimed in claim 6, wherein the biologically active material comprises iron, zinc, potassium, and salts of such metals, vitamin $B_{12}$, riboflavin, methionine, β-galactosidase, or bromelin.

8. A microgranular preparation as claimed in claim 1, wherein the polymer comprises a fatty acid.

9. A microgranular preparation as claimed in claim 8, wherein the fatty acid in the enteric coating comprises $C_{12-24}$ fatty acids.

10. A microgranular preparation as claimed in claim 1, wherein the biologically active material is selected from vitamins and vaccines.

11. A microgranular preparation as claimed in claim 1, wherein the biologically active material is selected from the group consisting of proteins and amino acids.

12. A microgranular preparation as claimed in claim 1, wherein the biologically active material is an enzyme.

13. A microgranular preparation as claimed in claim 1, wherein the alkali soluble acid-insoluble polymer comprises cellulose acetate phthalate.

14. A microgranular preparation as claimed in claim 1, wherein the insoluble polymer comprises butyl methylacrylate.

15. A microgranular preparation having a core comprising one or more biologically active materials, the core being concentrically encapsulated within a water-soluble, organic solvent-insoluble film consisting essentially of gelatin, and an enteric coating comprising a polymer which is insoluble in acid but soluble in alkali or intestinal juice, the microgranular preparation being packaged in combination with printed instructions for treating a condition or disease in a human or animal host by orally administering the microgranular preparation to the host.

16. A method for the production of a therapeutic microgranular preparation comprising the steps of:
   (a) immobilizing one or more biologically active materials within a core;
   (b) microgranulating the immobilized biologically active molecules;
   (c) encapsulating the microgranules with a water-soluble, organic solvent-insoluble film consisting essentially of gelatin; and,
   (d) coating the microgranules of step (c) with a polymer which is insoluble in acid but soluble in alkali or intestinal juice.

17. A method for increasing animal growth in pre-weaned animals, which comprises the administration of a growth-increasing effective amount of a microgranular preparation,
   said microgranular preparation having a core comprising immobilized β-galactosidase, the core being concentrically encapsulated within a water soluble film and an enteric coating comprising a polymer which is insoluble in acid but soluble in alkali or intestinal juice.

18. A method as claimed in claim 19, wherein the preweaned animal is a pig.

19. A method for the treatment of scour in piglets which comprises the administration of an amount, sufficient to be therapeutically effective in the treatment of scour, of a microgranular preparation,
   said microgranular preparation having a core comprising immobilized β-galactosidase or a protease, the core being concentrically encapsulated within a water soluble film and an enteric coating comprising a polymer which is insoluble in acid but soluble in alkali or intestinal juice.

20. A method as claimed in claim 19, wherein the protease is bromelin.

21. A method for the treatment of disease caused by pathogenic bacteria binding to intestinal receptors in man or another animal, which method comprises the administration of an amount, effective to treat said disease, of a microgranular preparation,
   said microgranular preparation having a core comprising immobilized β-galactosidase or a protease, the core being concentrically encapsulated within a water soluble film and an enteric coating comprising a polymer which is insoluble in acid but soluble in alkali or intestinal juice.

22. A method as claimed in claims 17, 19, or 21, wherein the gel matrix is formed from k-carrageenan, gelatin, alginate, cellulose or its derivatives, or synthetic polymers.

23. A method as claimed in claims 17, 19, or 21, wherein the microgranules have a size between about 25 and about 500 μm.

24. A method as claimed in claims 17, 19, or 21, wherein the microgranules have a size between about 50 and about 350 μm.

25. A method as claimed in claims 17, 19, or 21, wherein the polymer comprises a fatty acid.

26. A method as claimed in claim 25, wherein the fatty acid in the enteric coating comprises $C_{12-24}$ fatty acids.

27. A method as claimed in claims 17, 19, or 21, wherein the water soluble film comprises gelatin.

28. A method as claimed in claims 17, 19, or 21, wherein the alkali soluble acid-insoluble polymer comprises cellulose acetate phthalate.

29. A method as claimed in claims 17, 19, or 21, wherein the insoluble polymer comprises butyl methylacrylate.

* * * * *

UNITED STATES PATENT AND TRADEMARK OFFICE
CERTIFICATE OF CORRECTION

PATENT NO. : 5,356,625  Page 1 of 3
DATED : October 18, 1994
INVENTOR(S) : Thomas K.S. Ying It is certified that error appears in the above-indentified patent and that said Letters Patent is hereby corrected as shown below:

| COLUMN | LINE | |
|---|---|---|
| Title page: item [56] Pg. 1, col. 2 | Refs. Cited For. Pat. Docs. | Insert --36 655 1965 GDR-- |
| 1 | 38 | "region maybe" should read --region may be-- |
| 1 | 58 | "though" should read --through-- |
| 3 | 15 | "such" should read --such as-- |
| 6 | 51 | "cable" should read --capable-- |
| 7 | 28 | "sprayed" should read --spray-- |
| 7 | 38 | "in" should read --is-- |
| 8 | 9 | "if" should read --is-- |
| 8 | 49 | "bags" should read --bag-- |
| 8 | 61 | "disintergrated" should read --disintegrated-- |
| 9 | 31 | "transfer" should read --transferred-- |

UNITED STATES PATENT AND TRADEMARK OFFICE
CERTIFICATE OF CORRECTION

PATENT NO. : 5,356,625                      Page 2 of 3
DATED : October 18, 1994
INVENTOR(S) : Thomas K.S. Ying It is certified that error appears in the above-indentified patent and that said Letters Patent is hereby corrected as shown below:

| COLUMN | LINE | |
|---|---|---|
| 9 | 34 | Delete "Collect". |
| 9 | 40 | Insert "for" before --methionine content-- |
| 9 | 55 | "the" should read --The-- |
| 11 | 16 | "were, orally" should read --were orally-- |
| 11 | 30-31 | Delete "scouring: faeces liquid and profuse scouring, with evidence of debilitation and dehydration." and insert therefor: <br> --scouring:     faeces liquid and profuse <br>    severe        scouring, with evidence of <br>    scouring      debilitation and dehydration <br>    death:         -- |
| 11 | 39 | "has" should read --had-- |
| 12 | 47 | After "proteases" insert --may be used-- |

UNITED STATES PATENT AND TRADEMARK OFFICE
CERTIFICATE OF CORRECTION

PATENT NO.    :  5,365,625
DATED         :  October 18, 1994
INVENTOR(S)   :  Thomas K.S. Ying It is certified that error appears in the above-indentified patent and that said Letters Patent is hereby corrected as shown below:

COLUMN    LINE
   14          17          "claim 19," should read --claim 17,--
(Claim 18,  line 1)

Signed and Sealed this

Sixteenth Day of January, 1996

Attest:

BRUCE LEHMAN

Attesting Officer    Commissioner of Patents and Trademarks